(12) United States Patent
Dunne et al.

(10) Patent No.: US 9,089,658 B2
(45) Date of Patent: Jul. 28, 2015

(54) DISPENSING DEVICE, STORAGE DEVICE AND METHOD FOR DISPENSING POWDER

(75) Inventors: Stephen Terence Dunne, Stowmarket (GB); Marc Rohrschneider, Hagen (DE); Achim Moser, Sulzbach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 295 days.

(21) Appl. No.: 13/469,631

(22) Filed: May 11, 2012

(65) Prior Publication Data

US 2012/0222675 A1 Sep. 6, 2012

Related U.S. Application Data

(62) Division of application No. 11/576,853, filed as application No. PCT/EP2005/010768 on Oct. 6, 2005.

(30) Foreign Application Priority Data

| Oct. 6, 2004 | (GB) | 0422106.5 |
| Nov. 17, 2004 | (GB) | 0425289.6 |
| Dec. 15, 2004 | (GB) | 0427552.5 |
| May 4, 2005 | (GB) | 0509108.7 |

(51) Int. Cl.
*A62C 5/02* (2006.01)
*A61M 11/02* (2006.01)
*A61M 15/00* (2006.01)

(52) U.S. Cl.
CPC ........... *A61M 15/0028* (2013.01); *A61M 11/02* (2013.01); *A61M 15/002* (2014.02);

(Continued)

(58) Field of Classification Search
CPC .............. A61M 2202/064; A61M 15/0028; A61M 15/00; A61M 15/08
USPC ............ 128/203.24, 203.15, 200.23, 203.12, 128/203.21, 205.21; 239/337; 222/129
See application file for complete search history.

(56) References Cited

U.S. PATENT DOCUMENTS

| 4,681,258 A | 7/1987 | Jenkins et al. |
| 5,472,143 A | 12/1995 | Bartels et al. |

(Continued)

FOREIGN PATENT DOCUMENTS

| DE | 103 00 983 A1 | 7/2004 |
| GB | 2 323 042 A | 9/1998 |

(Continued)

*Primary Examiner* — Len Tran
*Assistant Examiner* — Adam J Rogers
(74) *Attorney, Agent, or Firm* — Roberts Mlotkowski Safran & Cole, P.C.; David S. Safran

(57) ABSTRACT

A dispensing device, and a method for dispensing powder in which powder is dispensed through a duct with a flat cross section to de-agglomerate the powder and to generate a spray with fine particle size. A storage chamber for the powder may be closed by a bursting element which is burst by pressurized gas for discharging the powder, the gas pressure reaching or exceeding a peak value before the bursting element bursts so that the powder is dispensed at a lower gas pressure. The powder may be forced through the duct by a gas pressure of less than 300 kPa to de-agglomerate the powder and/or to generate the spray. The storage device can have multiple storage chambers and associated ducts or nozzles, so that each dose of powder can be dispensed through a separate duct or nozzle, the storage chamber and duct or nozzle being formed of a one-piece construction.

20 Claims, 9 Drawing Sheets

(52) U.S. Cl.
CPC ....... *A61M15/0003* (2014.02); *A61M 15/0031* (2014.02); *A61M 15/0033* (2014.02); *A61M 15/0045* (2013.01); *A61M 15/0048* (2014.02); *A61M 15/0051* (2014.02); *A61M 2202/064* (2013.01); *A61M 2205/073* (2013.01); *A61M 2205/8225* (2013.01); *A61M 2206/16* (2013.01)

(56) References Cited

U.S. PATENT DOCUMENTS

| | | | |
|---|---|---|---|
| 5,497,944 A | | 3/1996 | Weston et al. |
| 5,590,645 A | * | 1/1997 | Davies et al. ............ 128/203.15 |
| 5,622,166 A | * | 4/1997 | Eisele et al. ............ 128/203.12 |
| 5,702,362 A | * | 12/1997 | Herold et al. ................... 604/58 |
| 5,785,049 A | | 7/1998 | Smith et al. |
| 5,875,776 A | | 3/1999 | Vaghefi |
| 5,911,851 A | | 6/1999 | Bartels et al. |
| 5,921,237 A | * | 7/1999 | Eisele et al. ............ 128/203.21 |
| 5,988,163 A | * | 11/1999 | Casper et al. ............ 128/203.15 |
| 6,007,676 A | | 12/1999 | Bartels et al. |
| 6,029,663 A | * | 2/2000 | Eisele et al. ............ 128/203.21 |
| 6,032,666 A | * | 3/2000 | Davies et al. ............ 128/203.15 |
| 6,089,228 A | | 7/2000 | Smith et al. |
| 6,123,068 A | * | 9/2000 | Lloyd et al. .............. 128/200.24 |
| 6,123,070 A | | 9/2000 | Bruna et al. |
| 6,273,086 B1 | | 8/2001 | Ohki et al. |
| 6,371,111 B1 | | 4/2002 | Ohki et al. |
| 6,408,846 B1 | | 6/2002 | Ohki et al. |
| 6,503,362 B1 | | 1/2003 | Bartels et al. |
| 6,543,448 B1 | | 4/2003 | Smith et al. |
| 7,013,894 B2 | | 3/2006 | McFarland, Jr. |
| 7,025,058 B2 | | 4/2006 | Armstrong et al. |
| 7,051,734 B2 | | 5/2006 | Casper et al. |
| 7,373,938 B2 | | 5/2008 | Nichols et al. |
| 7,984,713 B2 | | 7/2011 | Hochrainer et al. |
| 2002/0033177 A1 | * | 3/2002 | Ohki et al. ............... 128/203.15 |
| 2002/0092523 A1 | * | 7/2002 | Connelly et al. ......... 128/203.15 |
| 2003/0163099 A1 | * | 8/2003 | Wermeling et al. ........... 604/275 |
| 2003/0183229 A1 | * | 10/2003 | Smith et al. .............. 128/203.12 |
| 2005/0263151 A1 | | 12/2005 | Hochrainer et al. |

FOREIGN PATENT DOCUMENTS

| | | | |
|---|---|---|---|
| GB | 2 375 308 A | | 11/2002 |
| GB | 2375308 | * | 11/2002 |
| WO | 92/12799 A1 | | 8/1992 |
| WO | 02/053215 A2 | | 7/2002 |
| WO | 2004041326 A2 | | 5/2004 |

* cited by examiner

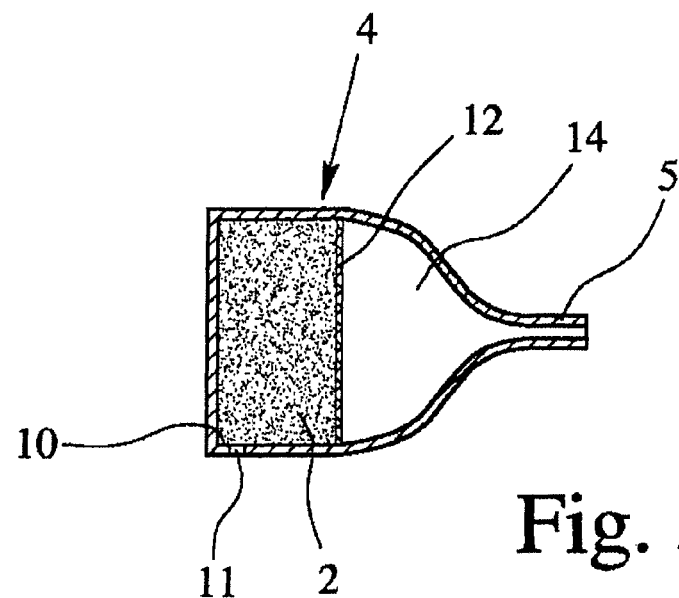
Fig. 5
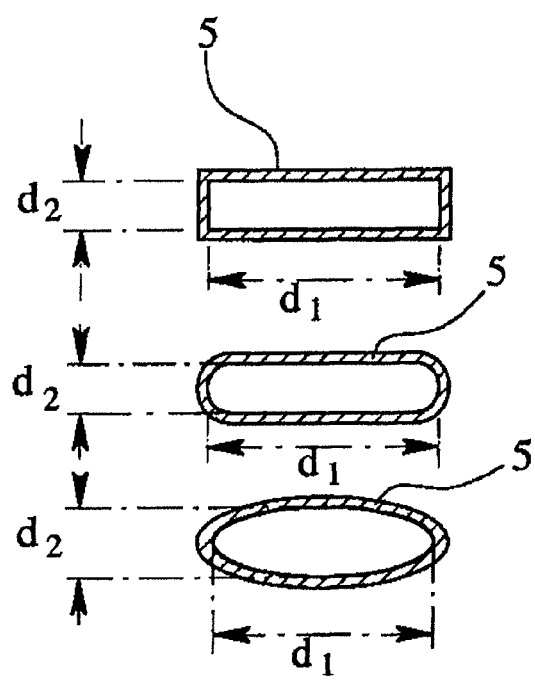
Fig. 6a
Fig. 6b
Fig. 6c

DISPENSING DEVICE, STORAGE DEVICE AND METHOD FOR DISPENSING POWDER

CROSS REFERENCE TO RELATED APPLICATION

This application is a divisional of co-pending U.S. patent application Ser. No. 11/576,853.

BACKGROUND OF THE INVENTION

1. Field of the Invention

The present invention relates to a dispensing device for dispensing powder, in particular, containing or consisting of a drug, as a spray including fine powder particles, and to a storage device for such powders which has at least one, and preferably, multiple separate storage chambers, each containing a single dose of the powder to be dispensed by gas pressure. The invention also relates to a method for dispensing a spray including fine powder particles by means of gas pressure.

2. Description of Related Art

Powder drugs delivered through dispensing devices, in particular, inhalers, are intended to optimally target specific sites in the pulmonary system. These sites include the nasal passages, the throat, and various locations within the lungs, such as the bronchi, bronchioles and alveolar regions. The ability to deliver drugs to a target area depends, inter alia, on the aerodynamic sizes of the particles. As currently believed to be understood, particles having an aerodynamic diameter of less than 2 µm are considered to be potentially optimal for deposition in the alveolar region of the lung. Particles that have an aerodynamic diameter of between 2 and approximately 5 µm may be more suitable for delivery to the bronchiole or bronchi regions. Particles with an aerodynamic size range greater than 6 µm, and more preferably, 10 µm, are typically suitable for delivery to the laryngeal region, throat or nasal passages.

In most cases, it is desired to achieve a high inhalable fraction and a high delivery efficiency, i.e., the fraction that reaches the desired region, in particular, in the lung. This depends on various factors, in particular, on the characteristics of the generated spray plume, such as propagation velocity of the plume, particle size and its distribution, fraction of small particles, fraction of gas and the like. In the present invention, the desired spray plume characteristics include preferably, a small particle size, a high fraction of drug particles with a diameter of 6 µm or less, a low propagation velocity, a long duration of spray generation and/or possible inhalation, and/or a low amount of gas volume required for dispensing a certain amount of powder.

In particular, the present invention is concerned with dry powder inhalers for the delivery of drugs to the lungs. Many dry powder inhalers are on the market or have been proposed. There are two main types, namely the passive ones and the active ones. In passive inhalers, all the energy required for de-agglomerating the powder and transferring the powder to the lungs is provided by the breathing of a user or patient. In active inhalers, there is an additional source of energy to help to de-agglomerate the powder.

Most powder inhalers are of the passive type where the powder is inhaled by the patient without the aid of an additional energy source. The problem with passive inhalers is that the inhalable fraction, or the proportion of powder that actually enters the lungs, is largely dependant on the breathing of the patient. The de-agglomeration of the powder and hence the inhalable fraction is a function of the flow rate of inhaled air through the device and, therefore, varies greatly from patient to patient.

Dry powder inhalers are subdivided into single dose devices and multi-dose inhalers. Multi-dose inhalers are further subdivided into pre-metered types where the doses are stored individually and into metering inhalers where the powder dose is metered in the device.

Multi-dose pre-metered inhalers have the advantage that the single doses are metered under strict factory conditions and the powder can quite easily be isolated from the atmosphere. In many applications, the active duct powder is mixed with a carrier, such as lactose which tends to absorb humidity from the atmosphere which makes it stick together and difficult to de-agglomerate.

The present invention relates, in particular, to an active, gas powered, pre-metered multi- or single-dose dispensing device for dispensing powder containing or consisting of a drug, such as a dry powder inhaler.

International Patent Application Publication WO 92/12799 A1, which forms the starting point of the present invention, discloses a pre-metered dispensing device for transforming a flow of fluid into a spray of fine particle size, wherein an annular flow through a duct is caused with a velocity gradient within that flow sufficient to cause sheer forces between components of the flow to break the flow up into a spray. The cross-sectional shape of the duct is preferably, circular, but other cross-sectional shapes, for example, an irregular cross section or a polygonal cross section can be used. However, the known device and method are not optimal for de-agglomerating the powder and for generating a slow spray plume with the desired characteristics.

International Patent Application Publication WO 2004/041326 A2 disclose a tubular nozzle for use in systems for delivering medicaments, in particular, for metering devices for dispensing liquid aerosols, i.e., so-called metered dose inhalers (MDIs). The tubular nozzle is curvilinear throughout a defined length and has a curved portion with a radius of curvature of at least 2.5 times the inner diameter of the tubular nozzle. The cross section of the tubular nozzle may be selected from a wide range of choices such as circular, oval, square, rectangular, polygonal, and the like.

SUMMARY OF THE INVENTION

A primary object of the present invention is to provide an improved dispensing device, storage device and method for dispensing powder, in particular, wherein better de-agglomeration of the powder and/or the desired spray plume characteristics can be realized.

The above object is achieved by a dispensing device as described below.

The dispensing device or the storage device may be adapted for dispensing subsequently multiple doses of powder. According to an independent aspect of the present invention, each dose may use a different duct or nozzle. In this way, buildup of powder in duct corners or blocking does not affect performance.

One aspect of the present invention is to provide a duct with a flat cross section. The powder is forced through the duct by pressurized gas to de-agglomerate the powder and to generate a spray including fine powder particles. The ratio of the largest side to the smallest side of the flat cross section of the duct is at least 2.0. Surprisingly, a much better de-agglomeration and finer particles can be achieved, in particular, with a lower amount of gas for a given volume or mass of powder, than by a circular or quasi-circular duct. This effect may be explained in that the flat cross section provides a larger perimeter for a given cross-sectional area than a non-flat cross section. This larger perimeter results in a larger duct surface that is in contact with the gas and powder so that better de-agglomeration can be achieved due to higher sheer forces without changing the cross-sectional area (hydraulic diameter), i.e., without changing the flow resistance or mass flow significantly.

Preferably, the ratio of the largest side to the smallest side of the flat cross section is between 3 to 50, and most preferably, is about 5 to 30. Thus, a high output of powder with good de-agglomeration as a spray with small powder particles size can be achieved by a comparatively low gas pressure, low gas volume, and low gas flow rate. The dispensing device produces a plume of de-agglomerated dry powder with a high inhalable fraction and with the desired spray plume characteristics.

It was found that, with fine powders of mean particles of fewer than 5 µm, a substantially rectangular duct of typically 75 µm by 1500 µm works well. With powders of mean particle size above 30 µm, a duct of typically 200 µm by 1500 µm works well. The noncircular duct should preferably, have a hydraulic diameter of between 20 to 1000 µm depending on the particle size of the powder. The duct can be made of any material that is drug compatible including plastics or metals. More than one noncircular duct may be used in parallel.

The noncircular duct, preferably, has a length of at least 5 or 10, preferably, between 10 and 60, hydraulic diameters (the hydraulic diameter is defined as the ratio of 4 times the cross-sectional area divided by the duct perimeter). For any given pressure, the longer the noncircular duct, the slower is the powder delivery to the patient. However, if the duct is too long, the velocity in the storing/mixing chamber may be reduced to an extent that the mixing chamber is not emptied.

In particular, it is possible to force the powder through the duct by a gas pressure of less than 300 kPa to de-agglomerate the powder and to generate the spray with fine particle size so that optimal spray plume characteristics, in particular, a low propagation velocity, can be achieved.

It is advantageous to minimize the exit velocity of the gas and powder in order to minimize powder impaction in the mouth and upper respiratory tract. However, the higher the exit velocity, the better is the powder break up or de-agglomeration. One solution to this situation is to slow the exit velocity of the gas and powder mixture at the duct exit by using two or more impinging ducts or powder jets which preferably, impinge at an angle of between 30° and 180°, preferably, 90° and 150°. This is another aspect of the present invention. In particular, multiple—at least two—powder spray jets are impinged, i.e., hit each other, to slow down the propagation velocity of the spray and/or to de-agglomerate the powder. This supports the desired spray plume characteristics as mentioned above. Alternatively, a diffuser with an increasing cross section may be used to decelerate the gas and powder flow at the exit of the duct.

Any gas may be used. For instance, liquefied gases, such as HFA134a and HFA227 may be used. In such a device, the gas is stored in a pressurized canister containing a metering valve with means connecting it to the powder reservoir(s). Alternatively, a piston cylinder arrangement, a bellows or any other gas pump may be used for pressurization, e.g., atmospheric air. In such a device, the user or patient needs to cock or prime the device prior to use. Further, compressed gas may be used. For single dose devices, a pre-pressurized canister of compressed air may be used.

The volume of gas needed to completely empty a storage chamber (reservoir) and/or mixing chamber depends on the powder volume or mass. For powder masses of 0.1 mg to 50 mg, gas masses of between 0.2 mg and 300 mg are required. For instance 5 mg of powder with a mean particle size of 4 µm requires between 10 cm$^3$ and 20 cm$^3$ of compressed air at between 100 kPa and 200 kPa with a mass of approximately 20 mg to 60 mg of air. For coarser powders, less gas volume is needed at a lower pressure, typically under 100 kPa gauge since less energy is required for de-agglomeration.

The volume of the storage chamber (reservoir) and optional mixing chamber needed to expel all the powder depends on the powder volume or mass. Preferably, it should have a volume of between 0.002 cm$^3$ and 0.2 cm$^3$ depending on powder dose. The larger the powder dose, the larger the reservoir/mixing chamber should be. For instance with a powder dose of 5 mg, a volume of between 0.015 and 0.03 cm$^3$ is needed for thorough mixing. Preferably, the ratio of the chamber volume (volume of the storage chamber and of the optional mixing chamber) to the powder volume should be between 1.2 and 4.

The reservoir should preferably, be of cylindrical shape with no sharp edges as these can attract powder deposits. The gas inlet or inlets should preferably, be positioned so that the gas sweeps all the chamber surfaces to prevent powder accumulating on the surfaces. Preferably, the inlet(s) should be placed near the chamber end furthest from the outlet, i.e., the noncircular duct. The relative positions of the entry(s) and outlet in the reservoir and mixing chamber may be arranged in such a way that the gas powder mixture forms turbulent eddies within the chamber to maximize de-agglomeration or that a smooth non-turbulent flow is achieved in the chamber(s).

Preferably, surface areas after the noncircular duct are minimized to minimize powder adherence or loss on said surfaces. The invention has the advantage that little or no powder is retained in the device after inhalation, and hence, the metered and delivered masses are almost the same.

Preferably, the noncircular duct should be located at a mouthpiece entrance with no flow restrictions after the noncircular duct.

According to another independent aspect, the storage chamber for a dose of powder may be closed by a bursting element or another pressure sensitive element designed such that the pressurized gas can burst the bursting element or open the pressure sensitive element for discharging powder from the storage chamber. In particular, the mixture of gas and powder only passes through the preferably, non-circular duct, a nozzle or the like after the gas pressure has reached a peak value, wherein the mixture is discharged by a lower gas pressure. This may be achieved by using the pressure sensitive element, such as a valve, the bursting element, a diaphragm or the like.

Preferably, the bursting element is made of a thin plastic film, coated aluminum film or any other suitable material. The pressure sensitive element, e.g., the bursting element, may be placed before the storage chamber or after it, in particular, between the storage chamber for the powder and an adjacent mixing chamber.

Preferably, a separate pressure sensitive element or bursting element is used for each dose of powder, i.e., each storage chamber.

According to another independent aspect of the present invention, the powder is forced through the duct or a nozzle or the like by a comparatively low gas pressure of less than 300 kPa to de-agglomerate the powder and/or to generate the spray. Experiments have shown that such low pressures are sufficient for achieving good de-agglomeration and optimal for achieving a slow spray.

According to another independent aspect, the gas flow is restricted or controlled at the inlet side, and not at the outlet side during dispensing of the powder. This is, in particular, possible with the non-circular duct. Preferably, the gas inlet has a respectively small cross section that restricts or controls the gas flow during dispensing.

According to a further independent aspect, the dispensing device or storage device may contain at least two or three separate storage chambers for separate or different drugs/powders, which can be dispensed subsequently or simultaneously, and in the latter case, preferably, are mixed only during the dispensing.

According to a further independent aspect of the present invention, the separate drugs or powders can be mixed by impinging at least two powder jets.

Further aspects, advantages and features of the present invention will be an apparent from the following detailed description of preferred embodiments with reference to the accompanying drawings.

BRIEF DESCRIPTION OF THE DRAWINGS

FIG. 5 is a schematic sectional view of a storage device with a duct;

FIGS. 6a-6c are cross-sectional views of ducts with different cross sections;

DETAILED DESCRIPTION OF THE INVENTION

Figure 1:
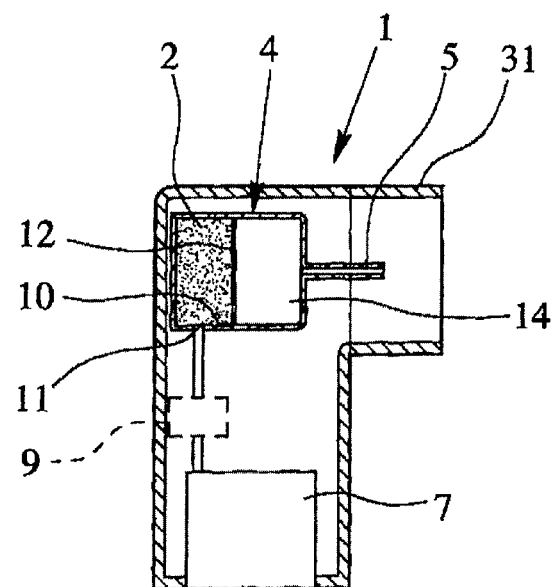
FIG. 1 is a schematic sectional view of a dispensing device according to one embodiment of the present invention.

In the drawings, the same reference signs are used for the same or similar components, wherein the same or similar characteristics, features or advantages are or can be realized or achieved, even if a repeated discussion is omitted. Further, the features and aspects of the different embodiments can be combined in any desired manner and/or used for other dispensing devices or methods for dispensing powder as desired.

FIG. 1 shows in a schematic cross section—for illustration purposes not in scale—of a dispensing device 1 according to the present invention. The dispensing device 1 is an active device, in particular, gas powered. Preferably, the dispensing device 1 is an inhaler, in particular, a dry powder inhaler, for a user or patient (not shown).

The dispensing device 1 is designed to dispense powder 2 which, in particular, contains or consists of at least one drug. The powder 2 may be a pure drug or a mixture of at least two drugs. In addition, the powder 2 may contain at least one other material, in particular, a carrier such as lactose.

Preferably, the mean diameter of the powder particles is about 2 to 7 µm, in particular, 6 µm or less. This applies, in particular, if the powder 2 does not contain any carrier, such as lactose.

If the powder 2 contains a carrier, such as lactose, and at least one drug, the powder 2 may have a particle size of 20 µm to 300 µm, in particular, about 30 µm to 60 µm. However, the de-agglomeration, which will be described later in more detail, may result even in this case in a spray 3 with a smaller particle size, e.g., of about 10 µm or less. In particular, the drug may be separated from the carrier during de-agglomeration so that primarily the drug will be inhaled due to its small particle size of about 2 µm to 6 µm and the larger carrier will be swallowed when using the dispensing device as an inhaler. Alternatively or additionally, breaking or opening of the carrier is possible during de-agglomeration.

The diameters mentioned above and below may be understood as mass medium aerodynamic diameters and/or may apply to the particle size or a fraction of the particles of the spray 3.

Figure 2:
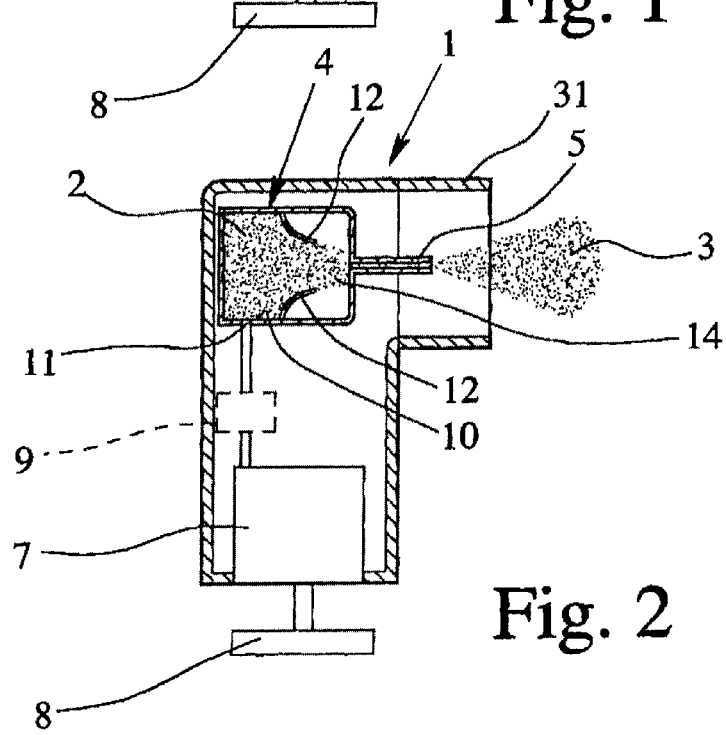
FIG. 2 is a schematic sectional view of the dispensing device according to FIG. 1 during dispensing.

FIG. 2 shows the dispensing device 1 when dispensing the powder 2 as a spray 3 in a very schematic manner similar to FIG. 1. The spray 3 comprises fine (powder) particles, i.e., has fine particle size of preferably, 6 µm or less. In particular, the spray 3 has the desired spray plume characteristics as described above.

The dispensing device 1 is adapted to receive or comprises a storage device 4 for storing the powder 2. The storage device 4 may be integrated into the dispensing device 1 or form part of the dispensing device 1. Alternatively, the storage device 4 may be a separate part, in particular, a container, cartridge, blister or the like that can be inserted or connected with the dispensing device 1 and optionally replaced.

The dispensing device 1 or the storage device 4 preferably comprises a duct 5 through which the powder 2 is dispensed for de-agglomerating the powder 2 and/or forming the spray 3.

Figure 3:
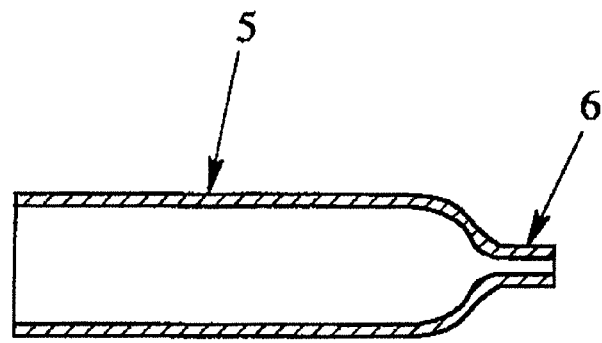
FIG. 3 is a schematic longitudinal sectional view of a duct with a nozzle.
Figure 4:
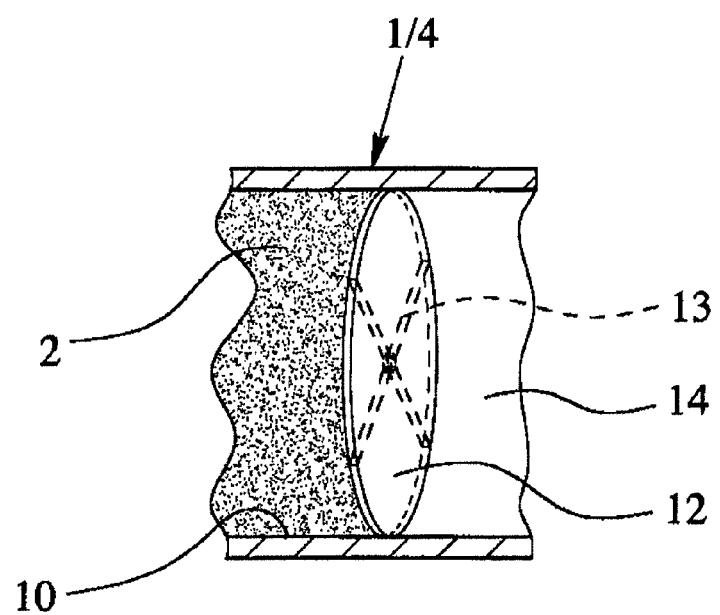
FIG. 4 is a partial sectional view of a storage chamber and a mixing chamber separated by a bursting element.
Figure 7:
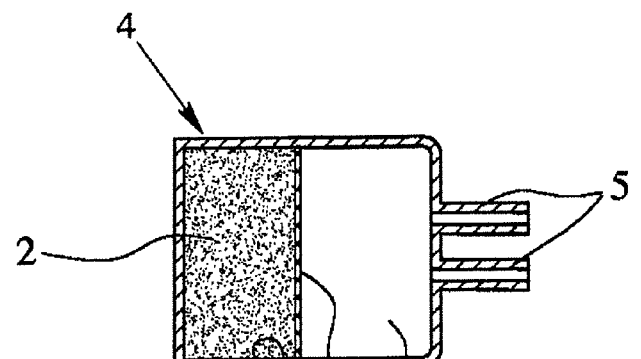
FIG. 7 is a schematic sectional view of a storage device with two ducts.

The duct 5 can comprise a nozzle (restriction) 6, preferably, at the outlet, as shown in schematic longitudinal cross section according to FIG. 3. Alternatively, the nozzle 6 or any other suitable nozzle arrangement could be used instead or in any other combination with duct 5.

The dispensing device 1 uses pressurized gas to force the powder 2 through the duct 5/nozzle 6 to de-agglomerate the powder 2 and/or to generate the spray 3 with fine particle size. Preferably, the dispensing device 1 comprises a means for providing pressurized gas which is an air pump 7 in the present embodiment, which can, preferably, be actuated or operated manually as indicated by handle or actuator 8. In particular, the air pump 7 comprises or is formed by a bellows. However, it could also be a piston-cylinder arrangement. Instead of the air pump 7, the means for providing pressurized gas can be, e.g., a capsule, container or the like containing pressurized or liquefied gas for powering the dispensing device 1, i.e., for dispensing the powder 2 as desired.

The air pump 7 may provide a gas pressure of less than 300 kPa, in particular, about 50 kPa to 200 kPa. This is, preferably, sufficient for operating the dispensing device 1. If liquefied gas or a container with pressurized gas is used, the gas pressures might range from 100 kPa to about 700 kPa. Then, the pressure may be reduced or throttled to the preferred pressure range before supplying the gas to the storage device 4, in particular, its storage chamber 10.

Preferably, all pressure values mentioned in the present description and the claims are gauge pressures, i.e., pressure differences. All pressure values relate to the pressure in a gas storage, such as a container with pressurized or liquefied gas or provided by air pump 7, or relate to the pressures acting in the chambers 10, 14 and/or in the duct 5, at least before a bursting element bursts as mentioned below.

Optionally, the dispensing device 1 comprises a regulator or control means 9 as indicated by dashed lines in FIGS. 1 & 2, in particular, a valve, a flow restrictor, a capillary tube or the like, for regulating, throttling and/or controlling the gas flow and/or pressure.

The dispensing device 1 or storage device 4 comprises at least one storage chamber 10 containing a single dose of powder 2 that is be dispensed in a single dispensing operation.

For dispensing, the gas is supplied under pressure to the storage chamber 10 via a gas inlet 11 or the like. Preferably, the inlet 11 is connected or connectable to the means for providing pressurized gas, i.e., in particular, the air pump 7, or to the regulator or control means 9.

In the present embodiment, the storage chamber 10 is, preferably, covered or closed by a bursting element 12. In particular, the bursting element 12 seals the powder 2 in the storage chamber 10 against humidity, air contact or the like.

When gas is supplied to the storage chamber 10, the bursting element 12 breaks or bursts if a predetermined pressure difference and/or a predetermined velocity of pressure increase is reached or exceeded (generation of a pressure pulse). Preferably, the bursting element 12 is designed to burst at a pressure difference of less than 300 kPa, more preferably, about 50 kPa to 200 kPa, and/or at a pressure pulse with a velocity of pressure increase of more than 0.5 MPa/s, in particular, more than 1 MPa/s.

The bursting element 12 can be made, e.g., of plastic or metal. It can be a thin foil, in particular, of aluminum, and/or any suitable membrane.

In the present invention, the bursting element 12 covers a cross-sectional area of the storage chamber 10 with a mean diameter of at least 5 mm, preferably, 7 mm or more.

Preferably, the bursting element 12 is pre-scratched or pre-scored or comprises at least one weakened portion to facilitate bursting, as indicated by reference sign 13 in FIG. 4 which is an enlarged perspective view of a portion of the storage chamber 10 with the bursting element 12. In particular, the bursting element 12 is arranged between the respective storage chamber 10 and an associated mixing chamber 14 as shown in FIG. 4.

When the bursting element 12 bursts or breaks, the storage chamber 10 is opened suddenly and the respective dose of powder 2 is dispensed, namely mixed with the gas, forced through the duct 5 and discharged as spray 3 as shown in FIG. 2.

The gas generates a flow in the storage chamber 10 sufficient to force all of the powder 2 through the outlet, i.e., duct 5. The mixing chamber 14 also forms an opening space for the optional bursting element 12, so that the bursting element 12 can open sufficiently when it bursts.

The bursting element 12 is intended to encompass, from the standpoint of the present invention, any pressure sensitive element that will rapidly open to allow gas flow through the storage chamber 10 for dispensing the respective powder 2 only if a certain gas pressure (peak pressure) is reached or exceeded. However, once the bursting pressure is reached and the bursting element 12 bursts or the pressure sensitive element opens, the gas expands and the pressure will significantly and/or suddenly drop so that the powder 2 may be mixed with the gas during a pressure pulse in a very effective manner, in particular, swirls or eddies support the mixing of gas and powder 2, but the powder 2 will be discharged—in particular, forced through the duct 5—with a lower, comparatively low gas pressure (preferably, less than 300 kPa, in particular, about 50 kPa to 200 kPa). This low gas pressure, which is significantly lower than the gas pressures in the prior dispensing devices, enables a respectively low discharge velocity and, therefore, a low spray 3 with low propagation velocity.

It is noted that the effect of the bursting element 12 can also be realized or supported or even increased by any other suitable pressure sensitive element, in particular, by a valve or by a respectively dimensioned reservoir for pressurized gas or the like.

The sudden expansion of the gas ensures good mixing of the gas and powder 2 in the chambers 10, 14 and, then, forces the mixture through the duct 5.

As already mentioned, the bursting element 12 is only optional. In some cases, the bursting element 12 is not required. Instead, a sealing element or the like may be provided which can be opened, e.g., just before dispensing the powder 2. Alternatively, the outlet end of the duct 5 and/or nozzle 6 could be closed for sealing the powder 2 in the storage chamber 10. Only for the dispensing operation is the duct 5/nozzle 6 opened, e.g., by cutting, piercing or the like, and then the powder 2 can be discharged.

According to another alternative, the duct 5/nozzle 6 could be closed by a suitable plug or cap which seals the powder 2 in the storage chamber 10 during non-use. This plug or cap could be removed just before the dispensing operation or opened by the gas pressure during the dispensing operation and have a similar function as the bursting element 12. In order to prevent inhalation of the plug, a respective filter could be provided or the plug could be connected in any suitable manner with another part so that the plug cannot separate totally.

Preferably, the storage device 4 forms the mixing chamber 14 for mixing the gas with the powder 2. The chambers 10, 14 are preferably, designed such that the gas can generate swirls or eddies for better mixing of the powder 2 with the gas. Preferably, the chambers 10, 14 are substantially circular in cross section, in particular, cylindrical. However, other shapes are also possible.

Further, the storage device 4, in particular, the chambers 10, 14, are formed with no sharp edges, corners or the like, but have a smooth contour so that the gas can sweep all chamber surfaces to prevent powder 2 accumulating on the surfaces and to ensure or allow complete discharge of the powder 2. In particular, the gas inlet 11 is located opposite the powder outlet, i.e., duct 5 and/or nozzle 6, with regard to the axial or outlet direction.

The storage device 4 may comprise only one storage chamber 10 for a single dose. In this case, the storage device 4 is for single dose only, or may comprise multiple storage cavities 10, and thus, contain multiple doses of powder 2, which can be dispensed subsequently.

The gas supply provided by the dispensing device 1, in particular, air pump 7, can be connected in any suitable manner to the respective storage device 4 or storage chamber 1, in particular, to the respective gas inlet 11, preferably, only temporarily when required for a dispensing operation. For example, a piercing element, connecting element or the like can be fluidically connected with gas inlet 11 respective storage chamber 10, in particular, by pushing it through a respective sealing element, diaphragm, membrane, wall portion or the like to open or enable gas supply to the respective storage chamber 10.

FIG. 5 shows, in a very schematic sketch, another embodiment of the storage device 4 or storage chamber 10, wherein the side walls, in particular, the ones of the mixing chamber 14, have a cross section that tapers towards the duct 5 in order to avoid any sharp edges, corners or the like where the powder 2 may remain despite the gas flow.

According to one aspect of the invention, the duct 5 has a flat (inner) cross section. FIGS. 6a to 6c show some of the suitable cross sections for the duct 5. FIG. 6a shows a substantially rectangular cross section. FIG. 6b shows a flat cross section with two opposite straight sides connected by two curved portions. FIG. 6c shows an oval or elliptical cross section.

In the present invention, a cross section is considered to be flat when the ratio of the largest side (width) d1 to the smallest side (height) d2 of the cross section is at least 2.0. Preferably, the ratio is from 3 to 50, and in particular, from about 5 to 70. It is pointed out that the cross sections shown in FIG. 6 are not to scale.

The largest side d1 is preferably, between 0.5 to 5 mm, in particular, 1 to 3 mm. Most preferably, the ratio of the largest side d1 to the (desired) fine particle size (mass mean diameter of the powder particles or drug particles of the spray 3) is less than 500, preferably, less than 300, in particular, about 30 to 300.

The smallest side d2 is preferably, between 0.05 to 0.5 mm, in particular, is about 0.07 mm to 0.25 mm. Most preferably, the ratio of the smallest side d2 to the mass mean (desired) fine particle size (mass mean diameter of the powder particles/drug particles of the spray 3) is less than 50, preferably, less than 30, in particular, about 3 to 20.

The length of the duct 5 means the length with the flat cross section. Thus, the duct 5 can have a larger length, i.e., further portions with another cross-sectional shape and/or with a larger cross-sectional area so that the influence of these other portions is low on the mixture of gas and powder 2 in comparison to the portion of the duct 5 with the flat cross section. However, the cross section area and/or the shape of the flat cross section may vary over the length of the duct 5 (the portion with the flat cross section). Thus, it is possible that the cross-sectional area of the duct 5 tapers from the inlet to the outlet or vice versa.

Most preferably, the duct 5 comprises at least one portion of flat cross section with constant cross section area, i.e., constant diameter and/or shape.

The length of the duct 5—i.e., the portion with flat cross section—may be in the range of 3 mm to 80 mm, in particular, 5 to 15 mm. Preferably, the duct length is adapted to the mean hydraulic diameter of the duct 5 such that the ratio of the length of the duct 5 to the mean hydraulic diameter is at least 5, in particular, about 10, preferably, 20 to 60, or more, wherein the hydraulic diameter is defined as the ratio of four times the cross-sectional area divided by the duct perimeter.

The diameter of the preferably, circular or cylindrical or conical chambers 10, 14 depends on the volume of mass of the respective dose of powder 2. A single dose may have, e.g., 1 to 2 mg (pure drug without carrier) or 2 to 10 mg (blend of drug with carrier, in particular, lactose). In the first case, the range of the diameter is preferably, 1.5 to 2.5 mm. In the second case, the range of the diameter is preferably, between 2 and 5 mm. Preferably, the cross section of the duct 5 varies in a similar manner. For example, the smallest side d2 is about 0.07 to 0.1 mm in the first case and about 0.15 to 0.25 mm in the second case. The larger (inner) side d1 does not depend so strongly on the powder or particle size. Preferably, it is in the range of about 1 to 2 mm in the first case and 1 to 3 mm in the second case.

The mean hydraulic diameter of the duct 5 is preferably, less than 1 mm, in particular, 0.1 mm to 0.6 mm.

Preferably, the duct 5 is molded and/or formed by a flat groove with a cover.

The dispensing device 1 or storage device 4 may comprise multiple ducts 5 for dispensing simultaneously one dose of powder 2, in particular, for increasing the total mass flow or output of dispensed powder 2 so that a desired dose can be discharged or dispensed in a sufficiently short time as desired and/or required.

FIG. 7 shows another embodiment of the storage device 4 in a schematic representation similar to FIG. 5. Here, two ducts 5 are associated or connected to one storage chamber 10/mixing chamber 14.

FIG. 8 shows, in a similar representation, a further embodiment, wherein the mixing chamber 14 and the ducts 5 are formed by a part that is separate from the storage device 4 and the storage chamber 10. This separate part can form a cover 15 or the like and is placed in contact with the storage device 4 or over the bursting element 12 before gas is supplied and the powder 2 is dispensed. The separate part may have only one duct 5 or it can have multiple ducts 5, in particular, two ducts 5 as shown. Multiple ducts 5 have the advantage that, even if one duct 5 is blocked, the dispensing device 1 still works, e.g., powder 2 can be still dispensed.

When the storage device 4 comprises multiple storage cavities 10 with respective doses of powder 2, the separate part covering the outlet side of the storage device 4 can be moved from one storage/mixing chamber 10/14 to the next one for subsequent discharge of the powder 2 from one storage chamber 10 after the other.

FIG. 9 shows another embodiment similar to FIG. 7, but with a multiplicity of ducts 5 which are preferably, arranged one directly at the side of the other so that a filter is formed in which the filter pores are formed by the ducts 5.

FIG. 10 shows a different embodiment of the storage device 4. In this embodiment, instead of a bursting element 12, the storage chamber 10 is closed by a sealing element or the like that can be opened, e.g., pierced, by the duct 5 (as shown in FIG. 10) or in any other suitable manner and connected with the duct 5 and/or nozzle 6. In this embodiment, a separate mixing chamber 14 is not provided. Instead, the storage chamber 10 has a volume that is not completely filled by the powder 2 so that the gas and the powder 2 can be mixed directly within the storage chamber 10, i.e., the storage chamber 10 also forms the mixing chamber.

Another aspect of this embodiment is that the direction of gas supply and the outlet of the mixing chamber 14 do not have to be transversal as it is the case in the previous embodiments. Instead, the gas inlet direction and the outlet direction from the storage chamber 10 may be in parallel planes, but preferably, offset with respect to each other and/or parallel to each other.

Figure 10:
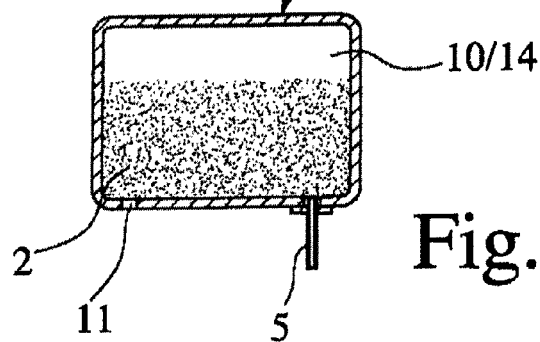
FIG. 10 is a schematic cross-sectional view of a storage device without bursting element.

FIG. 10 shows the dispensing device 1 or storage device 4 with duct 5 already inserted or connected. However, in FIGS. 5 & 7 to 10, the air supply is not yet connected to the storage chamber 10 or its inlet 11.

Figures 11, 12:
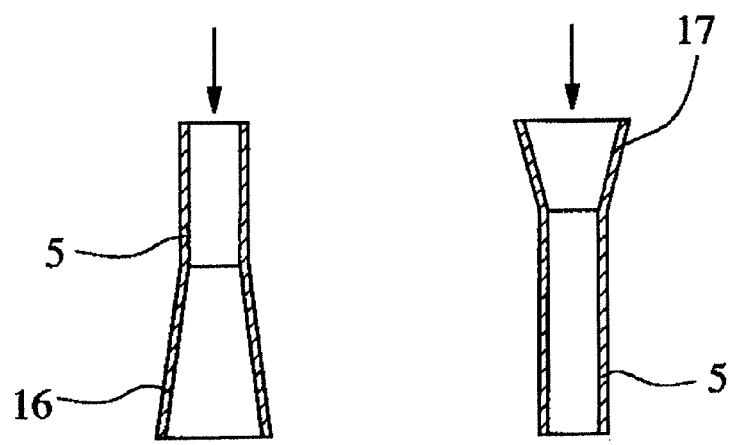
FIG. 11 is a schematic longitudinal sectional view of a diffuser.
FIG. 12 is a schematic longitudinal sectional view of a duct with a tapered inlet section.

FIG. 11 shows a longitudinal sectional view of another embodiment of the duct 5. Here, the dispensing device 1, or in particular, the duct 5 comprises a means for slowing down the outlet velocity and, thus, the propagation velocity of the spray 3. In this embodiment, the means for slowing down the velocity is a diffuser 16 located at or connected to the exit of the duct 5. The diffuser 16 has an appropriate angle to decrease the outlet velocity.

Additionally or alternatively, the duct 5 can also comprise a tapered inlet section 17 as shown in FIG. 12 in a longitudinal section view similar to FIG. 11. The tapered cross section 17 can have any suitable inner contour and may be curved to avoid any sharp edges at the transition to the taper section 17 or from the tapered section 17 to the duct 5. The tapered inlet section 17 may be used for all embodiments with a duct 5 or multiple ducts 5. This applies also for the embodiment according to FIG. 11, i.e., the means for slowing down the outlet velocity.

FIG. 13 is a schematic sectional view of another duct arrangement with another means for slowing down the velocity which forms a multiple powder jet spray impinging means 18. The impinging means 18 forms multiple—at least two—powder spray jets P which impinge, i.e., hit each other as indicated in FIG. 13. In this embodiment, the duct 5 divides into two sections 5*a*, 5*b* that are designed such that their openings or outlets are angled toward each other so that the powder jets P ejecting from the sections 5*a*, 5*b* are inclined relative to each other and impinge. For example, a flow divider 19 or any guiding means can be located in the flow path to form the at least two sections 5*a*, 5*b* of the duct 5 as shown in FIG. 13.

The impinging angle $\alpha$ between the powder jets P is between 30° to 180°, preferably, at least 90°, in particular, about 90° to 150°. The impinging of the powder jets P results in a decrease of the velocity of the spray 3 and/or in a de-agglomeration of the powder 2 and/or in separation of drug particles from a carrier and/or in better focusing of the spray 3. These effects depend on the impinging angle $\alpha$. A larger impinging angle $\alpha$ results in better effects. In contrast to liquid jets, an impinging angle $\alpha$ of 90° and more is possible and preferred. These angles also apply for the following embodiments.

The duct 5 is preferably, at least tangentially connected to the storage chamber 10 and mixing chamber 14 in the embodiment shown in FIG. 13. Preferably, the duct 5 is connected to the mixing chamber 14 at an axial end of the cylindrical chamber 14, and the gas inlet 11 is connected to the opposite axial end of the chamber 10. In particular, the gas inlet 11 is connected also tangentially to the storage chamber 10, such that swirls are generated when the gas enters with a swirl direction supporting discharge of the mixture of gas and powder 2 through the duct 5 which connects tangentially to the rotational direction of the swirl.

FIG. 14 shows a schematic sectional view of another embodiment of the powder jet impinging means 18. Here, two or more ducts 5 comprise inclined outlet sections 5*c* which are angled relative to each other so that the powder jets P ejected from outlet sections 5*c* impinge with each other.

FIG. 15 is a schematic sectional view of a further embodiment of the powder spray jet impinging means 18. Here, the ducts 5 are generally inclined relative to each other to achieve the designed impingement of the powder jets P. As shown, it is possible that the inlets of the inclined ducts 5 open at the side walls of associated mixing chamber 14 or storage chamber 10, optionally being formed between the sidewalls and a flow divider 19 located within the mixing chamber 14 or storage chamber 10 to ensure a desired flow and mixture of the gas with the powder 2.

The embodiments according to FIGS. 13 to 15 are also suitable for impinging more than two powder jets P. For example, it is possible to have similar arrangements in the cross-sectional planes perpendicular to the drawing plane resulting in, e.g., four outlet directions and powder jets P arranged on the surface of a conus. However, multiple other arrangements with similar effects are possible.

It is also noted that the cross sections of the duct sections 5*a* to 5*c* are, preferably, not flat but can have any suitable cross-sectional shape.

According to another embodiment (not shown), the duct 5 can also be used as a reservoir (storage chamber 10) for the powder 2. In this case, the separate storage chamber 10 and mixing chamber 14 are not required. In this case, the duct 5 is designed to enable sufficient mixing of the gas with the powder 2 and sufficient de-agglomeration of the powder 2.

Preferably, the gas inlet 11 or the gas supply has a smaller cross-sectional area than the duct 5 or nozzle 6 so that the gas flow is determined by the inlet and not by the outlet side, i.e., not by the duct 5 or nozzle 6, during dispensing. Thus, the pressure reaches a peak value at the beginning of the dispensing operation just before the bursting element 12 or another pressure sensitive element opens. With opening of the bursting element 12 or any other pressure sensitive element, the sudden pressure decrease results in that the gas and powder 2 mix very well and quickly in the storage chamber 10 and mixing chamber 14. Then, the mixture of gas and powder 2 is forced by the already lower gas pressure through the duct 5 and/or any other suitable outlet such as nozzle 6, wherein the gas flow is controlled during this phase at least mainly by the cross section of the gas inlet 11 or any other restriction stream up of gas inlet 11. Due to the comparatively low gas pressure for discharging the powder 2 through duct 5 and/or nozzle 6, a low discharge velocity, and thus, a low propagation velocity of the spray 3 can be achieved. A good de-agglomeration of the powder 2 can be achieved by the flat cross section of the duct 5 even with a comparatively low discharge velocity in the duct 5. In addition, the means for slowing down the propagation velocity of the spray 3, in particular, the diffuser 16 or the powder jet impinging means 18, can be used to further decrease the propagation velocity of the spray 3.

Preferably, the spray 3 has a mean velocity (taken 10 cm from the outlet or mouthpiece) of less than 2 m/s, in particular, less than 1 m/s. Preferably, the mean duration of the spray 3 is at least 0.2 or 0.3 s, in particular, about 0.5 s to 2 s.

FIG. 16 shows another embodiment of the dispensing device 1 or storage device 4 with multiple storage cavities 10. In particular, the storage device 4 is a circular disc, in which storage cavities 10 are positioned spaced from each other along the perimeter of the disc, preferably, with a radial orientation so that the associated mixing chambers 14 are located radially outwardly and/or adjacent to the storage cavities 10 and separated by respective bursting elements 12.

The disc may be of molded plastic or made in any other suitable manner or of any other suitable material that will not react with the intended contents. The storage cavities 10 and/or the mixing chambers 14 can have a cylindrical or conical form. The bursting elements 12 are preferably, disc-shaped and secured, for example, by conical holders 20 or the like in place covering the respective storage chamber 10, preferably, radially. The holders 20 may be secured, e.g., by an outer ring 21 or the like.

Figure 16:
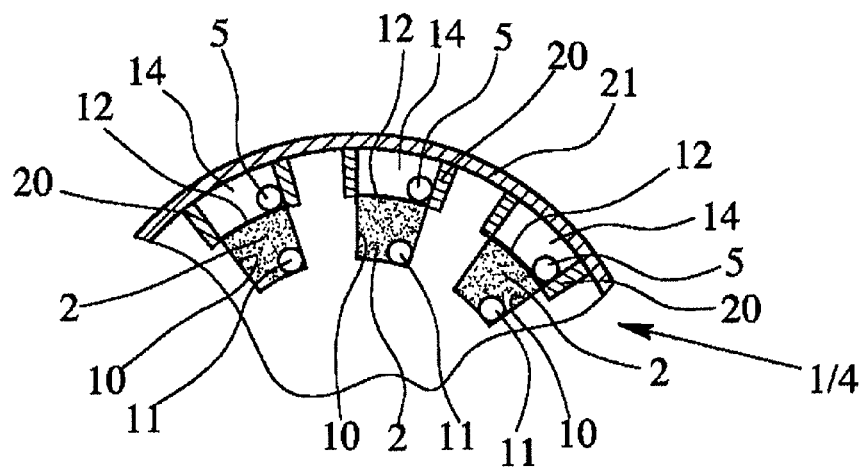
FIG. 16 is a schematic partial view of another storage device.

FIG. 16 shows the disc without a top cover or with a transparent cover that covers and closes the storage cavities 10 and the mixing chambers 14 from above. However, the gas inlets 11 and the duct 5 or other suitable outlet ports are formed in the cover and/or the disc or inserted just for the dispensing operation as depicted in FIG. 16. Alternatively, respective inlet ports and/or ports are formed in the disc.

For dispensing a dose of powder 2, the gas inlet 11 or a respective connection element and the duct 5 or a respective connection element are pushed through the sealing cover in the respective ports. Then, the gas supply is open or the air pump 7 is actuated, the bursting element 12 bursts and the gas pressure forces the gas powder mixture through the connected duct 5 and/or nozzle 6. Afterwards or just before the next dispensing operation, the disc is rotated to the next position.

Figure 17:
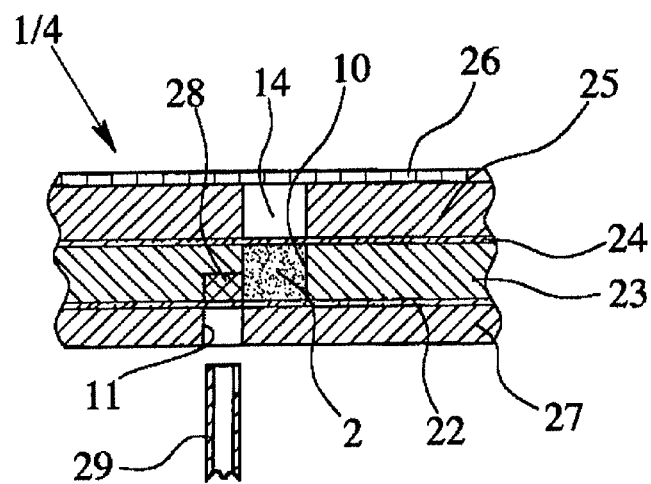
FIG. 17 is a schematic partial sectional view of a further storage device.

FIG. 17 shows a partial axial section of a similar dispensing device 1 or storage device 4 with multiple powder reservoirs (storage cavities 10). Preferably, it is a circular or cylindrical arrangement with some layers or discs placed axially one above the other. The powder 2 is completely shielded from atmospheric humidity (this applies to each embodiment), and thus kept dry.

In the embodiment shown in FIG. 17, a first sealing layer 22, preferably, made of foil, in particular, a thin coated aluminum foil, acts as a humidity barrier and covers the powder 2 in the respective storage cavities 10 on one axial side. The storage cavities 10 may be formed in a first disc 23, e.g., made of plastic. The first sealing layer 22 is preferably, bonded to the first disc 23. At the other side, a second sealing layer 24 is bonded to the first disc 23 and covers the storage cavities 10 from the other side and, thus, forms the bursting elements 12. The second layer 24 is preferably, also a foil, in particular, a thin coated aluminum foil or the like, and acts as a second humidity barrier for isolating the powder 2 in the storage cavities 10.

The second sealing layer 24, in turn, may be covered by a second disc 25 with recesses forming the respective mixing chambers 14 located axially above the associated storage cavities 10 separated by the second sealing layer 24.

A filter layer 26 or any other suitable cover may be bonded on the second disc for covering the mixing chambers 14. This layer 26 or cover may directly form the ducts 5, the nozzle 6 or any other suitable outlet means, such as a mesh. Alternatively, layer 26 may be a support and/or seal for an outlet element, such as the duct 5, that can be inserted into the respective mixing chamber 14 through layer 26 for the respective dispensing operation.

A third disc 27 may be bonded to the first sealing layer 22 on the side opposite the first disc 23. This third disc 27 can be made, e.g., of plastic, and have recesses or the like forming the gas inlets 11. These gas inlets 11 are, preferably, offset with respect to the storage cavities 10 so that transversal or tangential gas supply is possible instead of an axial gas supply.

Soft sealing elements 28 are preferably, arranged in the first disc 23 opposite to the gas inlet 11. For the dispensing operation, a gas supply element 29 or any other suitable element is pushed into a gas inlet 11 and through the first sealing layer 22 until the corresponding soft sealing element 28 is sufficiently deformed to allow ingress of gas into the associated (adjacent) storage chamber 10. When the gas supply is opened, e.g., flow regulator or control means 9, or the air pump 7 (see, FIGS. 1 & 2) is actuated and the pressure reaches a peak level, the respective bursting element 12 formed by the second layer 24 and the gas and powder mixture is forced through filter layer 26 or any other suitable output element, such as a duct 5 or nozzle 6.

It has to be pointed out that the third disc 27 is optional. For example, the gas inlets 11 could be formed in the first disc 23, in particular, between the first sealing layer 22 and the soft sealing element 28, or omitted.

Figures 18A, 18B:
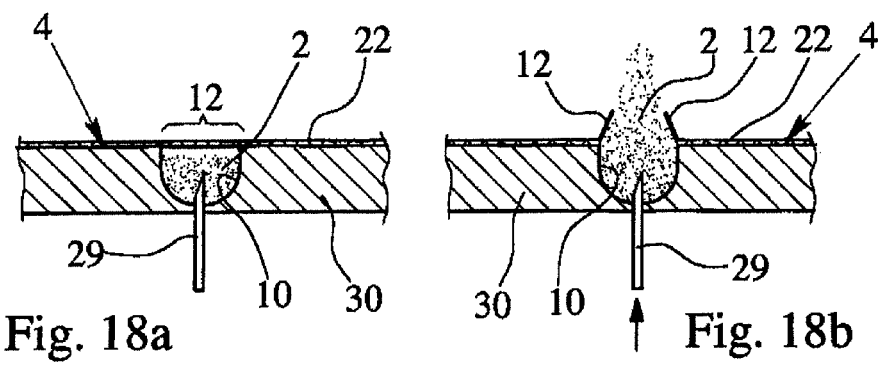
FIGS. 18a & 18b are schematic partial sectional views of a still further storage device before and during dispensing powder.

Further, it is possible to puncture or open a wall of the storage chamber 10 directly as shown in relative to the embodiment of FIGS. 18a & 18b in which the dispensing device 1 or storage device 4 comprises a base 30 with at least one storage chamber 10 or multiple storage chambers 10. In the latter case, the storage chambers 10 are preferably, arranged in a row, wherein the base 30 may form a strip, or along a circle, wherein the holder 30 may form a disc. A first sealing layer 22 covers the storage chamber(s) 10 and acts as a humidity barrier so that the powder 2 is isolated from the atmosphere and kept dry.

Figure 8:
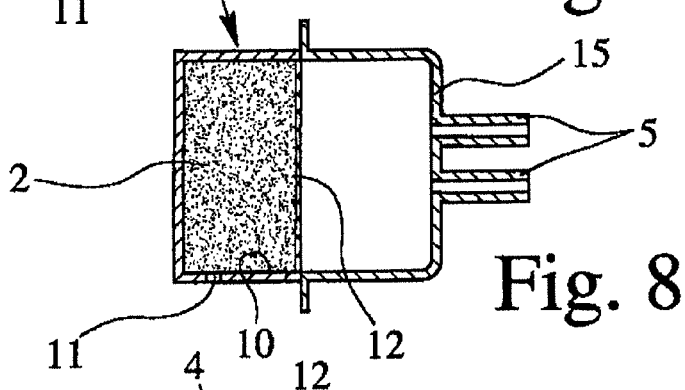
FIG. 8 is a schematic sectional view of a storage device and an associated cover with two ducts.
Figure 9:
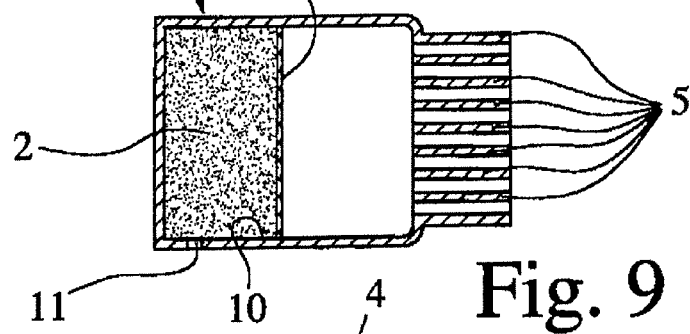
FIG. 9 is a schematic sectional view of a storage device with multiple ducts.

For the dispensing operation, the gas supply element 29 is pushed—for example, axially—through the base 30 or through a side wall or through the sealing layer 22 into the respective storage chamber 10 as shown in FIG. 18a. When gas is supplied and the gas pressure exceeds the bursting pressure, the layer 22, forming a bursting element 12, bursts and the powder 2 is discharged as shown in FIG. 18b. The powder 2 could be discharged into a cover 15 with at least one duct 5 as shown in FIG. 8, if that cover 15 is placed on the layer 22 above the respective storage chamber 10 before the gas is supplied.

Figure 19:
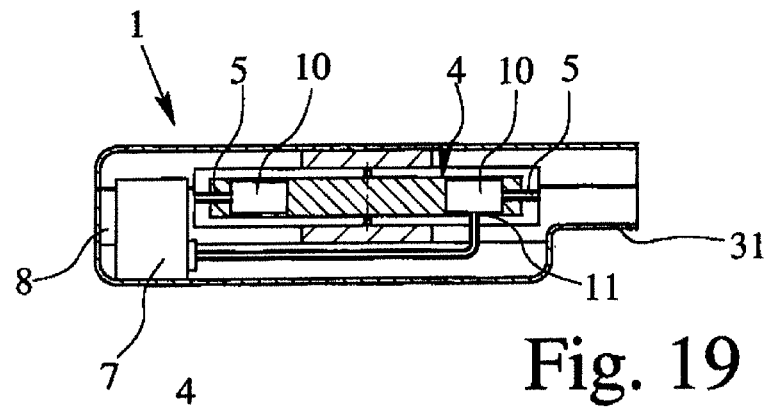
FIG. 19 is a schematic sectional view of a dispensing device according to another embodiment.

FIG. 19 shows another embodiment of the dispensing device 1 in a very schematic sectional view. In this embodiment, the storage device 4 is a, preferably, disc-like cartridge, container, blister or the like with multiple storage cavities. The storage device 4 can be rotated or indexed stepwise so that the powder 2 can be dispensed from the storage cavities 10, one after the other. In this embodiment, the gas may be supplied axially, and the mixture of gas and powder 2 may be dispensed radially, in particular, into a mouthpiece 31 for a user or patient (not shown). Preferably, the powder 2 is dispensed through at least one duct 5 and/or a nozzle 6 which is located within the mouthpiece 31, and in particular, set back with regard to the opening of the mouthpiece 31. This applies preferably, also to the dispensing device 1 shown in FIGS. 1 & 2.

Figure 20:
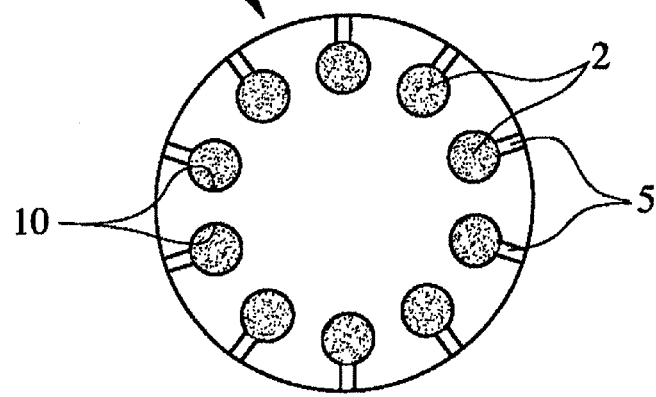
FIG. 20 is a schematic view of a storage device with radial ducts.

FIG. 20 shows a further embodiment of the storage device 4 with multiple storage cavities 10 in a circular or disc-like arrangement which could be used in the dispensing device 1 according to FIG. 19.

The storage device 4 comprises ducts 5 which may be oriented radially as shown in FIG. 20. This arrangement has the advantage that each dose of powder 2 may be dispensed through a separate, i.e., unused duct 5. If desired, a bursting element 12 may be arranged between each storage chamber 10 and the respective duct 5 as shown in FIG. 20. Further, a mixing chamber 14 may be associated with each storage chamber 10, in particular, between the bursting element 12 and the duct 5, if desired. Alternatively, each storage chamber 10 may also form the mixing chamber as already explained with respect to the embodiment according to FIG. 10. It is pointed out, that the features of the other embodiments, such as the powder jet impinging means 18 or the like, can also be realized in the embodiment according to FIG. 20.

Gas can be supplied, in particular, axially or tangentially into the storage cavities 10, e.g., by inserting a respective gas supply element 29 or the like, as in FIGS. 18*a* and 18*b*.

It is noted, that the present invention, in particular, the dispensing device 1 and/or the storage device 4, can be used for dispensing one drug, a blend of drugs or at least two or three separate drugs. In the latter case, the separate drugs are stored in separate storage chambers 10 and, during the dispensing operation, the drugs are mixed with the gas either in a common mixing chamber 14 or in separate mixing chambers 14 or in their respective storage chambers 10. Further, the separate drugs can be discharged through a common duct 5/nozzle 6, or through separate ducts 5/nozzles 6. In the latter case, the separate drugs will be mixed after leaving the separate ducts 5/nozzles 6 or in the mouthpiece 31 or in any other suitable (additional) mixing chamber. It is also possible to mix the separate drugs by impinging powder jets of the separate drugs. For dispensing the separate drugs, it is possible to use a common gas supply or means for pressurizing gas such as the air pump 7 or separate gas supplies/means for providing pressurized gas.

Figure 21:
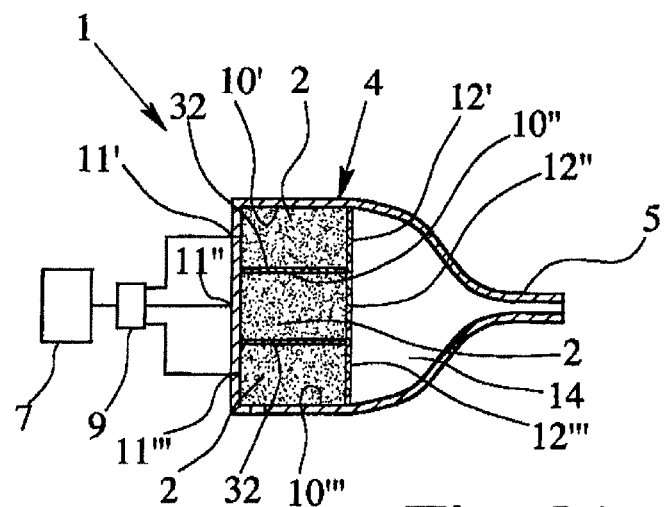
FIG. 21 is a schematic partial sectional view of another dispensing device and storage device.

FIG. 21 shows a further embodiment of the dispensing device 1/storage device 4 with at least two or three separate powders 2, i.e., separate drugs, which are stored in separate storage chambers 10', 10" and 10''', which may be formed by intermediate walls 32, and each storage chamber can be covered by an optional bursting element 12', 12" or 12'''. Pressurized gas can be supplied from a common means for providing pressurized gas, in particular, air pump 7 and/or regulation of control means 9, via separate gas inlets 11', 11" and 11'''. Alternatively, separate gas supplies can be provided.

When the gas pressure reaches the peak or burst pressure in the storage chambers 10', 10" and 10''', the respective bursting elements 12', 12" and 12''' burst and the separate drugs/powders 2', 2" and 2''' mix in the common mixing chamber 14 and the mixture is dispensed together through at least one common duct 5, nozzle 6 or the like as spray 3 (not shown in this figure).

It has to be noted that the bursting elements 12', 12" and 12''' can be formed from a common layer of material, in particular, foil or the like.

Alternatively, the central storage chamber 10" could be encompassed by at least one, preferably, annular storage chamber. In this case, wall 32 can be cylindrical and the reference signs 10' and 10''' would denote the same annular storage chamber resulting in only two different drugs/powders 2 in the two separate storage chambers (central chamber and annular chamber) in the embodiment of FIG. 21. In such a case, then the reference signs 12' and 12''' would relate to the same annular bursting element covering the annular chamber.

Figure 22:
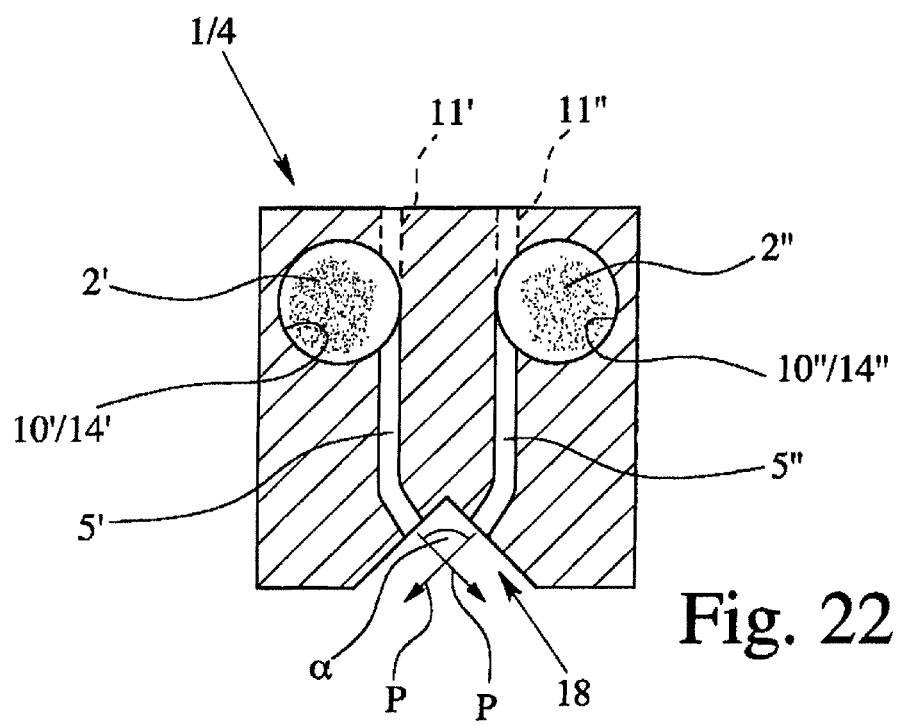
FIG. 22 is a schematic sectional view of a further dispensing device and storage device.

FIG. 22 shows, in a schematic sectional view, another embodiment of the dispending device 1 and storage device 4. Two different drugs/powders 2', 2" are contained in separate storage/mixing chambers 10'/14' and 10"/14", respectively. Gas can be supplied via separate gas inlets 11', 11" to the chambers 11'/14' and 10"/14", respectively. The powders 2', 2" can be dispensed and de-agglomerated by means of separate ducts 5', 5" or separate nozzles or the like (not shown). The powder jets P of the separate or different drugs/powders 2', 2" ejecting from the separate ducts 5', 5" are, preferably, impinged for mixing the separate drugs/powders 2', 2" just when forming the spray 3 (not shown in this figure). The powder jet impinging means 18 mixes the separate drugs/powders 2', 2", but can also serve to slow down the propagation velocity of the spray 3 and/or to support de-agglomeration of the powders 2', 2" or of separating the respective drugs from carriers.

In the following, two examples are described which show the effect of the present invention.

EXAMPLE 1

Figure 13:
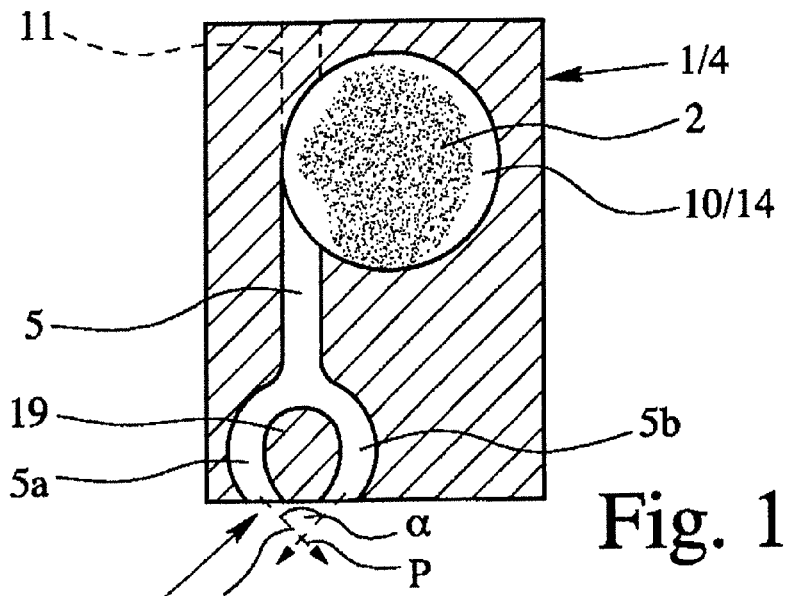
FIG. 13 is a schematic sectional view of a dispensing device and storage device with a multiple powder jet impinging means.
Figure 14:
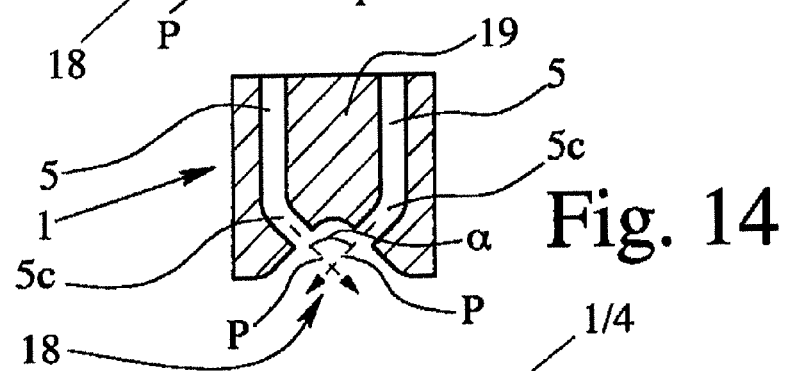
FIG. 14 is a schematic sectional view of another multiple powder jet impinging means.
Figure 15:
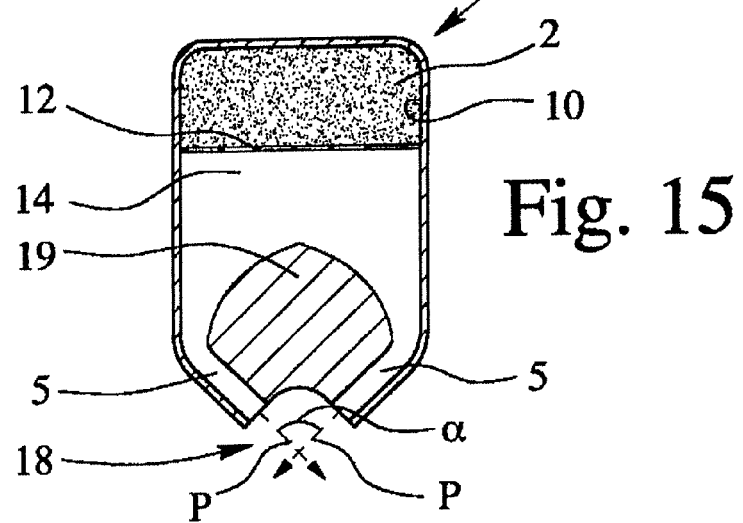
FIG. 15 is a schematic sectional view of a storage device with a further multiple powder jet impinging means.

A blend of 90.0% by weight of lactose 200, of 9.7% by weight of fine lactose, and of 0.3% by weight of Tiotropium was used. The mean particle diameter of lactose 200 was about 45 µm, of fine lactose about 4 µm and of Tiotropium about 4 µm. About 5.5 mg of the blend was positioned as powder 2 in the storage and mixing chamber 10/14 which had a substantially cylindrical shape with a diameter of 3 mm and an axial length of 3 mm. 5 ml of compressed air was supplied via the gas inlet having an inlet orifice of 0.5 mm into the chamber 10/14 with a gauge pressure of about 100 kPa. The powder 2 was dispensed via duct 5 of substantially rectangular cross section having a smallest side of about 0.18 mm and a largest side of about 1.5 mm. The duct 5 was divided into two duct sections 5*a*, 5*b* (in particular, as shown in FIG. 13), wherein each section had a substantially rectangular cross section with a smallest side of about 0.18 mm and the largest side of about 0.75 mm. The total length of the duct 5 including the sections 5*a*, 5*b* was about 8 mm. The result was that 100% of the metered mass, i.e., all of the powder 2 in the chamber 10/14, was dispensed. Approximately 50% of both diameter mean and mass mean fine fraction was measured on a Anderson Cascade Impactor at both 30 and 60 l/min.

EXAMPLE 2

About 1.5 mg of Fenoterol with a mean particle diameter of 4 µm was positioned as powder 2 in the storage and mixing chamber 10/14 which had a substantially cylindrical shape with a diameter of 2 mm and an axial length of 2 mm. 5 ml of compressed air was supplied via the gas inlet having an inlet orifice of 0.5 mm into the chamber 10/14 with a gauge pressure of about 150 kPa. The powder 2 was dispensed via a duct 5 of substantially rectangular cross section having a smallest side of 0.075 mm and a largest side of 1.5 mm. The duct 5 was divided into two duct sections 5*a*, 5*b* (in particular, as shown in FIG. 13), wherein each section had a substantially rectangular cross section with a smallest side of about 0.075 mm and the largest side of about 0.75 mm. The total length of the channel including the sections 5*a*, 5*b* was about 8 mm. The result was that 100% of the metered mass, i.e., all of the powder 2 in chamber 10/14, was dispensed. Approximately 45% of both diameter mean and mass mean fine fraction was measured on a Anderson Cascade Impactor at both 30 and 60 l/min.

What is claimed is:

1. A dispensing device for dispensing a powder as a spray including fine powder particles, the dispensing device comprising a plurality of storage devices, each of which has a cylindrical shaped storage chamber containing a single dose of the powder to be discharged by gas pressure and at least one of a duct and a nozzle associated with a first end of each storage chamber so that each dose of powder is dispensed through the at least one of a duct and nozzle by the gas pressure supplied by means of a gas inlet located at an opposite second end of each storage chamber, wherein each storage device together with its storage chamber and associated at least one of a duct and nozzle is formed of a one-piece construction, and wherein the gas inlet is tangentially connected to the storage chamber.

2. The dispensing device according to claim 1, wherein each storage device is a separate part from the other of the plurality of storage devices.

3. The dispensing device according to claim 1, wherein an outlet end of the at least one of a duct and nozzle is closed for sealing the powder in the storage chamber.

4. The dispensing device according to claim 1, wherein the duct has a flat cross section, a ratio of a largest side of the flat cross section to a smallest side of the flat cross section being at least 2.0.

5. The dispensing device according to claim 1, wherein the duct is formed by a flat groove with a cover.

6. The dispensing device according to claim 1, wherein the gas inlet has a smaller cross-sectional area than the duct or nozzle so that the gas flow is determined by the inlet and not the outlet side during dispensing.

7. The dispensing device according to claim 1, further comprising an air pump for providing pressurized gas.

8. The dispensing device according to claim 7, wherein the air pump is actuated or operated manually by a handle or actuator.

9. The dispensing device according to claim 7, wherein the air pump is connectable to a gas supply element.

10. The dispensing device according to claim 9, wherein, for dispensing dose of the powder, the gas supply element is pushed into a gas inlet of a respective storage chamber through one of a sealing element, diaphragm, membrane, and wall portion to enable gas supply to the respective storage chamber.

11. The dispensing device according to claim 1, wherein each storage device comprises multiple storage chambers.

12. The dispensing device according to claim 1, wherein the storage devices are located in a circular carrier disc spaced from each other along the perimeter of the disc.

13. A method for dispensing powder, comprising the steps of:
providing at least one cylindrical chamber containing a fine powder, at least one of a duct and nozzle connected to a first end of said at least one cylindrical chamber,
pushing a gas supply element into a gas inlet through one of a sealing element diaphragm, membrane, and wall portion, the gas inlet being tangentially connected to an opposite second end of the at least one cylindrical chamber,
actuating an airpump, and
discharging the powder from the chamber by means of gas pressure directly through the one of a duct and nozzle as a spray.

14. A dispensing device for dispensing a powder as a spray including fine powder particles, the dispensing device comprising:
a gas supply element,
a plurality of storage devices, each of which has a storage chamber containing a single dose of the powder to be discharged through an outlet thereof by gas pressure supplied from said gas supply element, and
at least one of a duct and a nozzle through which each dose of powder is dispensed from said outlet;
wherein each storage chamber is of a cylindrical shape and has one of a sealing element and wall portion at a distance from said outlet, and
wherein said gas supply element is adapted to pass through said one of a sealing element and tangentially puncture a wall portion of the storage chamber for directing gas pressure into each storage chamber.

15. The dispensing device according to claim 14, wherein the duct or nozzle is connected to the storage chamber at an axial end of the storage chamber.

16. The dispensing device according to claim 14, wherein the gas inlet has a smaller cross-sectional area than the duct or nozzle so that the gas flow is determined by the inlet and not the outlet side during dispensing.

17. The dispensing device according to claim 14, further comprising an air pump for providing pressurized gas.

18. The dispensing device according to claim 17, wherein the air pump is actuated or operated manually by a handle or actuator.

19. The dispensing device according to claim 17, wherein the air pump is connectable to said gas supply element.

20. Dispensing device for dispensing a powder as a spray including fine powder particles, the dispensing device comprising a plurality of storage devices, each of which has a storage chamber containing a single dose of the powder to be discharged by gas pressure by means of a gas inlet and at least one of a duct and a nozzle associated with each storage chamber so that each dose of powder is dispensed through the at least one of a duct and nozzle by the gas pressure, and wherein each storage device together with its storage chamber and associated at least one of a duct and nozzle is formed of a one-piece construction, the gas inlet being offset with respect to the storage chamber for enabling a transverse gas supply.

* * * * *